(12) United States Patent
Levola

(10) Patent No.: US 6,758,563 B2
(45) Date of Patent: Jul. 6, 2004

(54) EYE-GAZE TRACKING

(75) Inventor: Tapani Levola, Tampere (FI)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 10/169,198

(22) PCT Filed: Dec. 13, 2000

(86) PCT No.: PCT/FI00/01091

§ 371 (c)(1),
(2), (4) Date: Oct. 28, 2002

(87) PCT Pub. No.: WO01/49167

PCT Pub. Date: Jul. 12, 2001

(65) Prior Publication Data

US 2003/0156257 A1 Aug. 21, 2003

(51) Int. Cl.$^7$ ................................................ A61B 3/14
(52) U.S. Cl. ...................................................... 351/209
(58) Field of Search ................................ 351/205, 209, 351/210, 211, 215, 200, 221, 246; 382/103, 117

(56) References Cited

U.S. PATENT DOCUMENTS 5,644,642 A * 7/1997 Kirschbaum ................ 382/103
5,982,555 A    11/1999 Melville et al.
6,027,216 A * 2/2000 Guyton et al. ............... 351/200

FOREIGN PATENT DOCUMENTS

| EP | 0 350 957   | 1/1990  |
|----|-------------|---------|
| WO | WO 99/36826 | 7/1999  |
| WO | WO 99/65381 | 12/1999 |

* cited by examiner

Primary Examiner—George Manuel
(74) Attorney, Agent, or Firm—Banner & Witcoff, Ltd.

(57) ABSTRACT

A device and a method for tracking an eye-gaze of an observer. A deep blue or violet light source is used to emit light to eye, particularly to the retina. The deep blue light is partially reflected and partially absorbed by the retina. The absorption is most prominent around the fovea, the area of sharp vision, because of the pigment which protects the fovea from short wavelength radiation. Thus the device and method of tracking eye-gaze according to the invention comprises emitting light having a certain wavelength and transferring the light to the retina of an eye. The wavelength of the light being such as to make the fovea of the eye resolvable. The method further comprises detecting light that is reflected from the eye to form detection information including the resolvable fovea, and mapping the detection information to a predetermined surface, the surface being located at a distance from the eye, the location of the fovea on the surface forming an eye-gaze point.

23 Claims, 5 Drawing Sheets

EYE-GAZE TRACKING

FIELD OF THE INVENTION

This invention relates to eye-gaze tracking and, more particularly to an eye-gaze tracking device and method preferably for tracking the eye-gaze of a user on a surface such as a display.

BACKGROUND OF THE INVENTION

Keyboards, mice or joysticks provide a communication interface between a human and an electronic device. Eye-gaze measurements have been used in physiological and psychological studies disclosed in document Arne John Glenstrup and Theo Engell-Nielsen: BS thesis, Laboratory of Psychology, University of Copenhagen which is available in Internet at the URL http://www.diku.dk/~panic/eyegaze/article.html. Further eye-gaze tells about an interest area of an observer.

Present eye trackers are based on reflections of Infra Red (IR) light from the different layers of the eye, which is known as Purkinje reflections, and on reflection from a retina, which is seen as a bright iris. There are trackers that use only Purkinje images and trackers that combine the reflections from cornea and bright iris. Those reflections move with respect to each other and with respect to the bright iris depending on gaze direction. Usually one IR point source is enough but in order to increase accuracy several IR sources have been used. The retina has very large reflection at red and even more at IR wavelengths. Also the visibility of details, e.g. blood vessels, vanish when using longer wavelengths. Thus the retina looks very uniformly illuminated. This is why the iris-cornea method uses IR wavelengths.

Present eye trackers face major drawbacks to be able to fulfill the need for general usage. Eye trackers that are based on the Purkinje and/or the so called iris-cornea method must be calibrated frequently and a calibration is user dependent. In addition of that, these devices are not suitable for all people, because the eye structure of some people is incompatible for the device. This is because of physiological differences in the eye, especially physiological differences in eyelid positions. Other concerns are slowness of the device, that is, a delay in the existing devices prevents the required control.

An additional drawback is a general eye tracking structure of present eye trackers. Present eye trackers are bulky and heavy on a system level. These eye trackers require systems which are too massive for intelligent integrated electronic devices such as displays, virtual reality computer displays, portal computers and mobile phones.

Present eye-gaze tracking methods monitor the outer parts of an eye. These methods are very much person dependent and they are too much affected by personal eye geometry or the position of eyelids. Thus personal differences of eye physiology set a restriction for a common usage. These methods are inaccurate for required controlling and tracking.

A need for an improved user interface setting hands free is evident, as the devices become smaller, portable, more intelligent and ubiquitous. Eye-gaze tracking should set a data stream delivering high information content to the part of a display the eye is gazing. Efficient monitoring of eye-gaze is inevitable to eye-gaze controlled communication between a human and an electronic device. A control set could be defined by eye-gaze itself or eye-gaze combined to other existing control sets, such as a button. In addition, an eye-gaze tracking/control device should provide a response with an imperceptible delay for a device user for required usage. Current devices do not meet these abilities or they provide infeasible implementations.

SUMMARY OF THE INVENTION

The present invention provides a device and a method for tracking an eye-gaze on a surface such as a display of an electronic device and thus provides a base for controlling the electronic device according to the eye-gaze of a user.

According to a first aspect of the invention there is provided a method of tracking eye-gaze, the method comprising emitting light having a certain wavelength;

transferring the light to the retina of an eye;

the wavelength of the light being such as to make the fovea of the eye resolvable;

detecting light that is reflected from said eye to form detection information including the resolvable fovea;

mapping the detection information to a predetermined surface, said surface being located at a distance from said eye, the location of the fovea on said surface forming an eye-gaze point.

According to a second aspect of the invention there is provided an eye-gaze tracking device, comprising:

a light source for emitting light having a certain wavelength;

means for transferring the light to the retina of an eye, the wavelength of the light being such as to make the fovea of the eye resolvable;

a detector for detecting light that is reflected from said eye to form detection information including the resolvable fovea;

a surface located at a distance from said eye; and means for mapping the detection information to the surface for locating the fovea on said surface for forming an eye-gaze point by the location of the fovea.

In a preferred embodiment of the invention a deep blue or more preferably violet light source is used to emit light into the eye, particularly to the eye retina. Accordingly this means light having a wavelength in the range of about 395–500 nm, where a violet light having a wavelength of about 395–430 nm is preferred but blue light up to a wavelength of about 480 nm also works. Further an optical x-y matrix detector is used to measure the light reflected from eye retina. From the reflected light the foveal position, which is the eye-gaze, with respect to the optical assembly is measured with the detector.

According to another embodiment of the invention an eye-gaze tracker is integrated to a display, which can be a virtual reality display.

In one embodiment of the invention, eye-gaze control can set a data stream delivering high information content to the part of a display that the eye is gazing. Also in an embodiment, a control set or a control master is eye-gaze combined to hand controlling equipment. According to an embodiment of the invention, there may be provided software which measures and calculates fovea from data received from the detector, preferably the x-y detector, which may be a CCD (Charge Coupled Device) for example. In a further embodiment, the invention is provided with a pattern recognition calculation of blood vessels and comparing the calculations with a calibration pattern of blood vessels.

The invention provides several advantages over prior solutions. For example, a device according to one method of the invention may be implemented to be a simple light eye-gaze tracking device. This enables an embodiment for Virtual Reality (VR) displays having a reasonable physical size. Moreover, for portable computers or mobile units, such as mobile phones, a device for eye-gaze tracking according to the invention of reasonable structure can be implemented.

Preferably tracking and detecting the eye-gaze is based on the observation of the retina. This follows that the invention functions for different eyes although personal physical eye structure may vary considerably. This allows a large amount of users to apply the invention. The invention is thus suitable for substantially all users having normal physical human eye structure.

Moreover, the observation of the retina gives reliable and precise information of eye-gaze. Eye-gaze direction can preferably be determined without calibration of the device. Thus it is possible to obtain eye-gaze position on a display within immediate reaction from the eye-gaze device having measured with the detector (such as a CCD detector) and mapped to a display, e.g. a LCD.

BRIEF DESCRIPTION OF THE DRAWINGS

The disclosed invention will be described with reference to the accompanying drawings, which show embodiments of the invention and where.

DETAILED DESCRIPTION OF THE PREFERRED EMBODIMENTS

The invention will be described with particular reference to a preferred embodiment. However, it should be understood that the different embodiments provide only a few examples of the many advantageous uses of the innovative teachings herein.

Figure 2B:
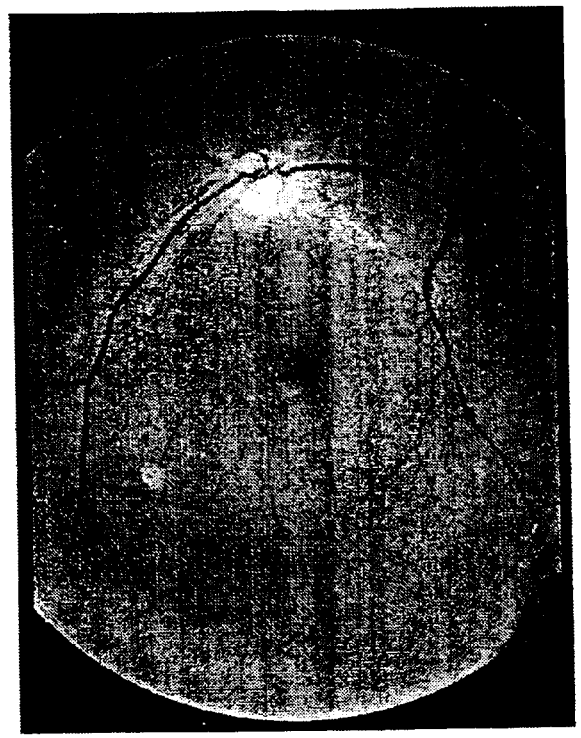
FIGS. 2a and 2b depict an elucidation for utilization about physical feature of retina of healthy eye at IR and at blue/violet wavelengths.
Figure 2A:
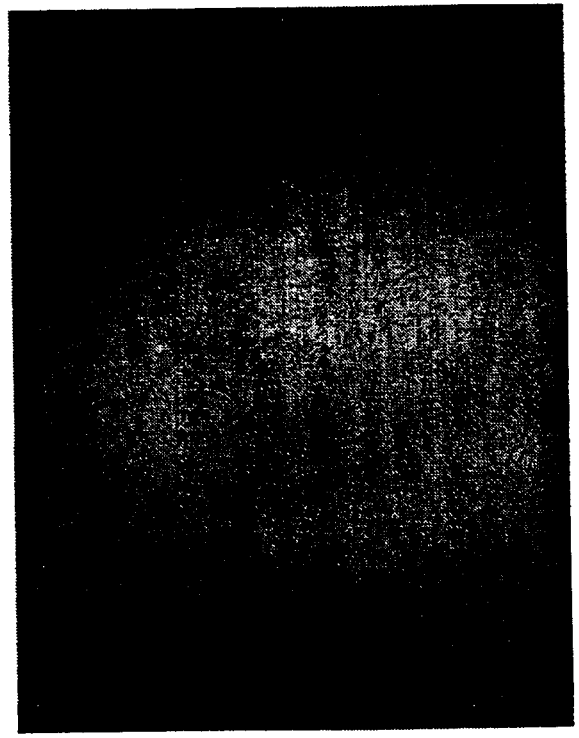

Various embodiments of the disclosed method and device will be described utilizing the physical feature of the retina. FIGS. 2a and 2b depict an elucidation for utilization about the physical feature of a retina of a healthy eye at IR (infrared) light and at blue light or violet light wavelengths, respectively. FIG. 2a shows the retina of a healthy eye illuminated at IR light wavelengths. The retina has very large reflection at red and even more in IR wavelengths. Also the visibility of details, e.g. blood vessels, vanish when using longer wavelengths. On the other hand when the wavelength is shortened, more and more details come out. Not only blood vessels but also fovea emerges. This can be seen from FIG. 2a where at IR light the fovea cannot be detected. FIG. 2b shows the retina of a healthy eye illuminated at blue wavelengths. At blue light the fovea emerges as a dark spot and the further we go to shorter wavelengths the more prominent the fovea is. Thus a deep blue or violet light sets a clear and prominent fovea. This is due to the UV protective pigment (xantofyllein-lutein), which is densest just in the fovea. The deep blue or violet light is partially reflected and partially absorbed by the retina. The absorption is most prominent around the fovea, the area of sharp vision, because of the pigment which protects the fovea from short wavelength radiation. This yellow pigmented area is called the macula lutea. Because of the absorption (whereas other parts of the eye reflect light at this wavelength) the fovea becomes resolvable as a dark spot. Accordingly this means light having a wavelength in the range of about 395–500 nm. A violet light having a wavelength of about 395–430 nm is preferred. When a light of longer wavelength is used the fovea does not anymore emerge very clear. The fovea has been detected by blue light having a wavelength of about 480 nm. Thus even a wavelength of 500 nm and a bit above still brings out the fovea but when moving closer to red light (600–700 nm) the fovea can no longer be detected as shown in FIG. 2a. The fovea does appear clearly also for light having a wavelength less than 395 nm, but that is not recommended as it may damage the eye. Thereby light with a wavelength of 395–430 nm is preferred, and good results have been achieved with 405 nm.

The eye tracking optics comprises a narrow band 118 beam splitter (implemented as a coating) and a deep blue or violet source 116 for illumination of the retina 100. In two passes through the quarter wave plate 122 (which also is narrow band, e.g. in the range of 405 nm), the polarization of the short wavelength light will rotate by 90 degrees but does not affect the other bands of spectrum (except the band of the quarter wave plate). The LCD panel 108 does not alter the polarization state of this short wavelength light. The illumination optics 114, polarizer 120, prisms 124 and 126 and the quarter wave plate 122 work so that the short wavelength light is guided to the retina 100. The short wavelength light, which is reflected from the retina, is going back to the device, but now the narrow band reflector 118 guides the light towards the detector 106. The focal plane of this light is inside the prism 126, and a relay lens 128 transforms the image from this plane onto the detector 106. The relay lens also takes care of correct scaling, because the display panel 108 and the detector 106 can have different dimensions. The detector 106 can be for example a CCD camera and is used to convert optical information to electronic or binary information. The LCD panel 108 is a reflective microdisplay and is used as a traditional displaying unit and as a function unit to set a location to eye-gaze. The display panel 108 can be also transmissive but in this case the illumination is assembled behind the panel. The light source can be implemented as a LED (Light Emitting Diode) and also the other optics shown in FIG. 1 (i.e. the parts except the display) can be made of small size and thus this may made in a size such as 18 mm×18 mm×6 mm.

Figure 1:
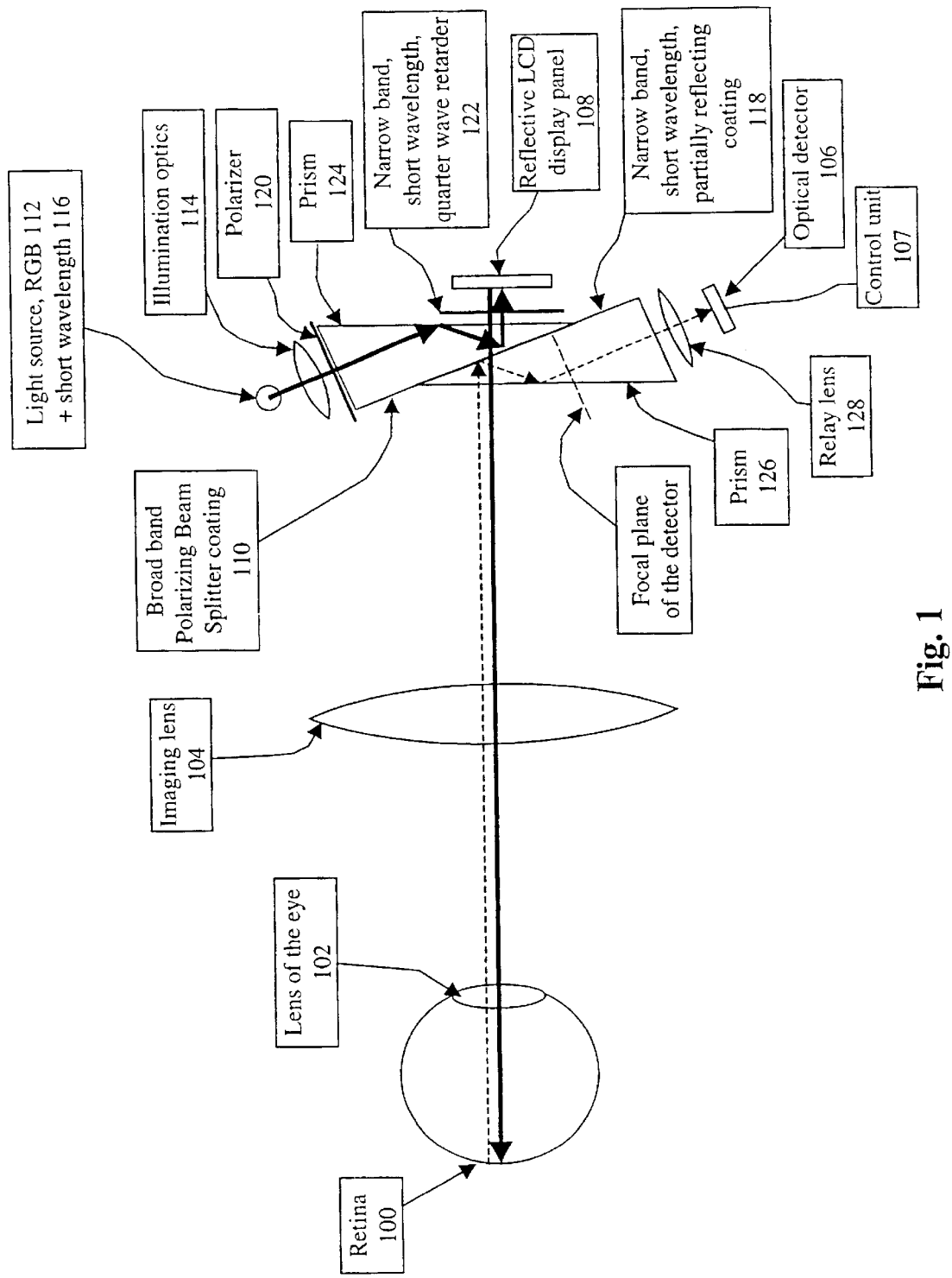
FIG. 1 depicts a block diagram of the device architecture of a preferred embodiment.

In the embodiment of FIG. 1, the imaging optics 104 transforms and transfers a picture of the LCD panel to a picture on the retina 100. This is done to achieve a clear picture on the retina 100. Thus the imaging optics 104 and also the lens of the eye 102 sets rays from the LCD panel 108 to the retina 100 in such a way that the picture on the retina 100 is visible and noticeable according to its source from the LCD panel 108. The illumination optics 114 is formed so that the LCD panel 108 has a homogeneous illumination and also so that the amount of short wavelength light 116 entering the eye is optimized, e.g., a safe amount of light that enters eye that causes no physical harm or damage to the eye. The short wavelength of light (~400 nm or at least less than 500 nm) can be so low of intensity or so short pulses used, that the human eye cannot resolve the light. Thus the eye tracking operation is not observed by the user whereas the detector can be built very sensitive to this part of light spectrum. Thus the light source 112 illuminates the LCD panel 108 homogeneously and has no considerable interference to the detection at the detector 106 about light reflected from the retina 100 to the detector 106. Also on the other hand, the short wavelength source 116 has no considerable interference to rays forming picture emitted by the LCD panel 108 to the retina 100. The deep blue or violet illumination is arranged so that it visible when the LCD panel 108 is homogeneously illuminated by deep blue or violet light. The image of retina is thus transformed on to the detector 106. There will be some stray light from the cornea, the iris, the pupil and the lens but these parts are not in focus and therefore they contribute only to background, thus having no considerable interaction to an observer.

In the embodiment of FIG. 1, the aim is to measure a location of a fovea on the detector 106. The fovea sets a one to one correspondence to an eye-gaze on surface, which eye is gazed and a fovea spot is detected and measured. A position of the fovea spot on the detector 106 has one to one correspondence to a position on the LCD panel 108. Thus measuring on the detector 106 a fovea spot, which is eye-gaze, utilizing one to one correspondence between the detector 106 and the LCD panel 108, a fovea spot on the LCD panel 108 is formed, which is now an eye-gaze on the LCD panel 108. The fovea spot appears as dark spot on the picture of the reflected light from the retina 100. Thus an aim is to measure this dark spot. The detector 106 detects and converts detection information to data, which is a numerical or electrical form of detection information. This data is transferred to a controller unit 107. Running software in control unit 107 measures and calculates the fovea spot from the data and transfers this information to the device using the display.

Alternatively, the location of a fovea may be obtained from CCD data, where a CCD detector is used as detector 106. Detection information and thus CCD data is obtained as described above. Also the entire VRD device can be corresponding as in the preferred embodiment. The location of a fovea from CCD data may be obtained by using a comparison of patterns. From CCD data an initial calibration pattern of blood vessels is formed in control unit 107. After a calibration pattern is set, a new measurement and thus a new CCD data of an eye-gaze position is detected on the CCD detector 106. From new CCD data a pattern of blood vessels is formed in the control unit 107. The control unit performs a series of functions to implement a pattern recognition calculation of these two patterns (pattern recognition by comparing a measured pattern with a calibration pattern being known as such). The control unit 107 performs a series of calculations to implement comparison between calibration pattern and eye-gaze pattern. By these calculations and a comparison (of the measured and calibration pattern) the control unit 107 sets the location of a fovea spot on the CCD detector 106. Mapping the location of a fovea, moreover eye-gaze, between the CCD detector 106 and the LCD panel 108 is implemented correspondingly as was described above, and yet by obtaining the fovea from CCD data using pattern comparison.

Figure 3:
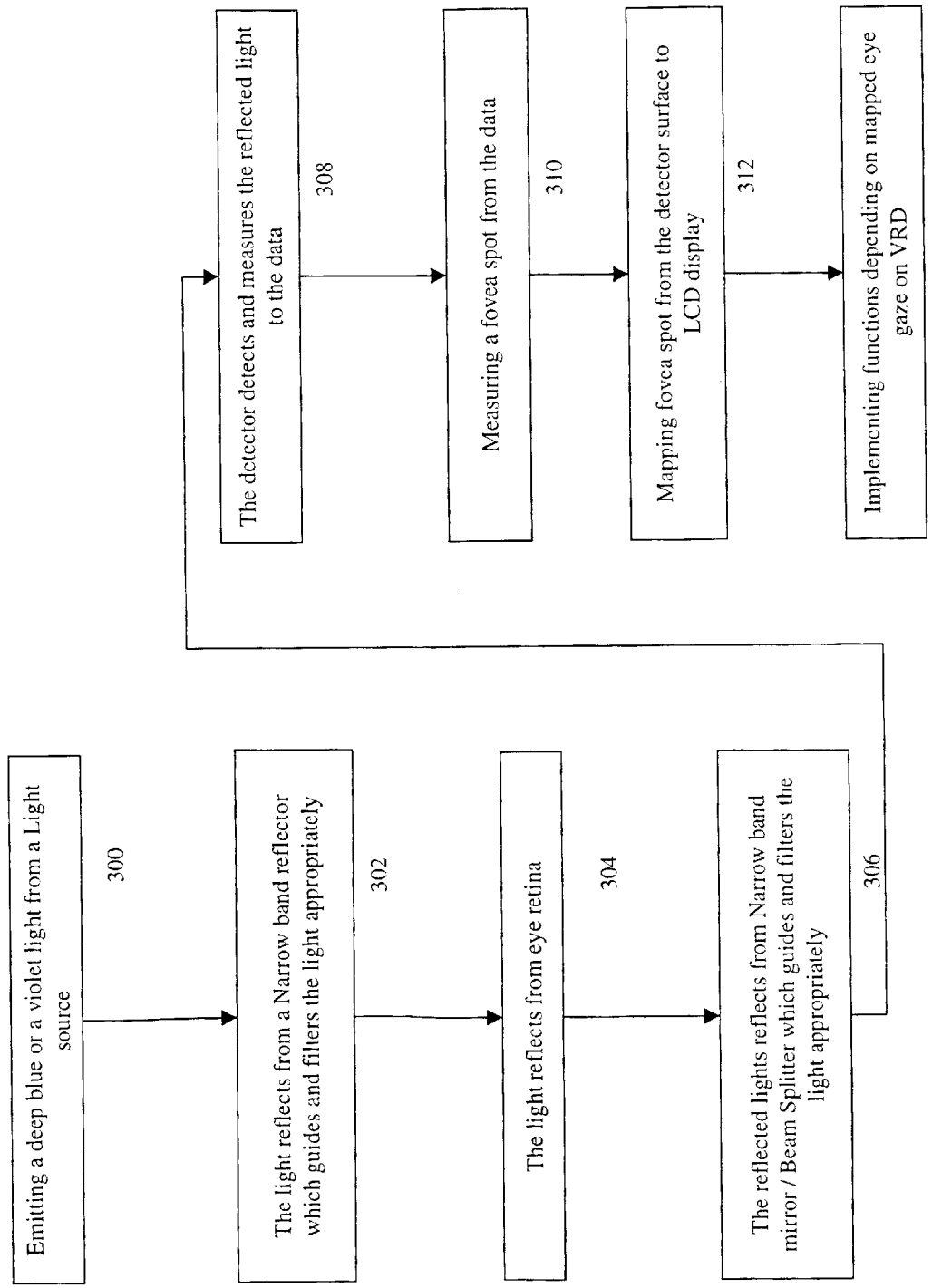
FIG. 3 depicts a flow chart of a preferred embodiment of a calibration free eye-gaze tracking.

FIG. 3 depicts a flow chart of an embodiment of the device and method of tracking eye-gaze according to the invention. A deep blue source 116 emits a deep blue or violet light (Step 300). A narrow band blue reflector 118 reflects the emitted light appropriately according to frequency and direction (Step 302). The emitted and reflected light reflects back from the eye retina (Step 304). Light reflected from the eye retina reflects from narrow band blue or violet beam splitter 118 appropriately according to frequency and direction (Step 306). A detector 106 detects the reflected light and converts this light detection information to electronic or binary data form (Step 308). The detector 106 measures a fovea spot from the data (Step 310). The control unit 107 maps the fovea spot from the detector 106 surface (Step 312). The device implements functions depending on mapped eye-gaze on VRD, e.g. display eye-gaze on LCD panel thus on VRD or set control to eye-gaze location (Step 314).

Figure 4:
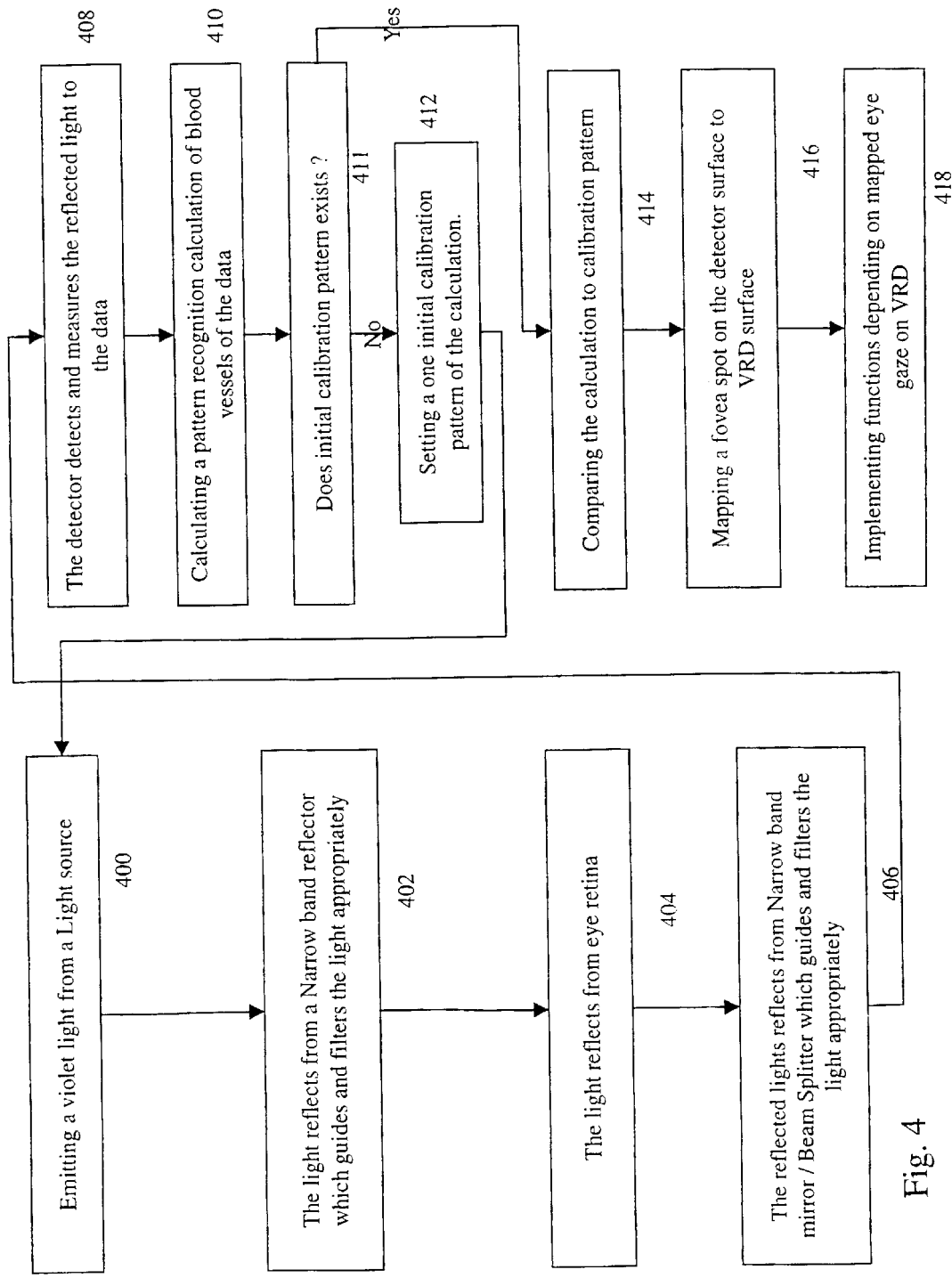
FIG. 4 depicts a flow chart of another embodiment of the eye-gaze tracking.

FIG. 4 depicts a flow chart of an alternative embodiment of the device and method of tracking eye-gaze according to the invention. A deep blue source 116 emits a deep blue or violet light (Step 400). A narrow band blue reflector 118 reflects the emitted light appropriately according to frequency and direction (Step 402). The emitted and reflected light reflects back from the eye retina (Step 404). Light reflected from the eye retina is further reflected from narrow band blue or violet beam splitter 118 appropriately according to frequency and direction (Step 406). A detector 106 detects the light reflected from the narrow band mirror 118 and converts the light detection information to electronic or binary data form (Step 408). The control unit 107 calculates a pattern recognition calculation of blood vessels from the data (Step 410). If an initial calibration pattern does not exists, the calculated pattern is set to form an initial calibration pattern (Steps 411 and 412). The device then sets a new CCD data from streaming eye-gaze information. If initial calibration pattern exists, the control unit 107 compares the calculation to calibration pattern (Steps 411 and 414). The control unit 107 maps the fovea spot from the CCD detector 106 surface to the LCD panel 108, thus to VRD surface (Step 416). The device implements functions depending on the mapped eye-gaze on VRD, e.g. display eye-gaze on the LCD panel thus on the VRD or sets control to eye-gaze location (Step 418).

Eye-gaze tracking/control should set a data stream delivering a high information content to the part of the display that the eye is gazing. Efficient monitoring of eye-gaze is inevitable to eye-gaze controlled communication between a human and an electronic device. A control set should be eye-gaze itself or eye-gaze combined to other existing control means such as a control button. In addition, an eye-gaze tracking/control device should provide a response with an imperceptible delay for a device user for required usage.

Figure 5:
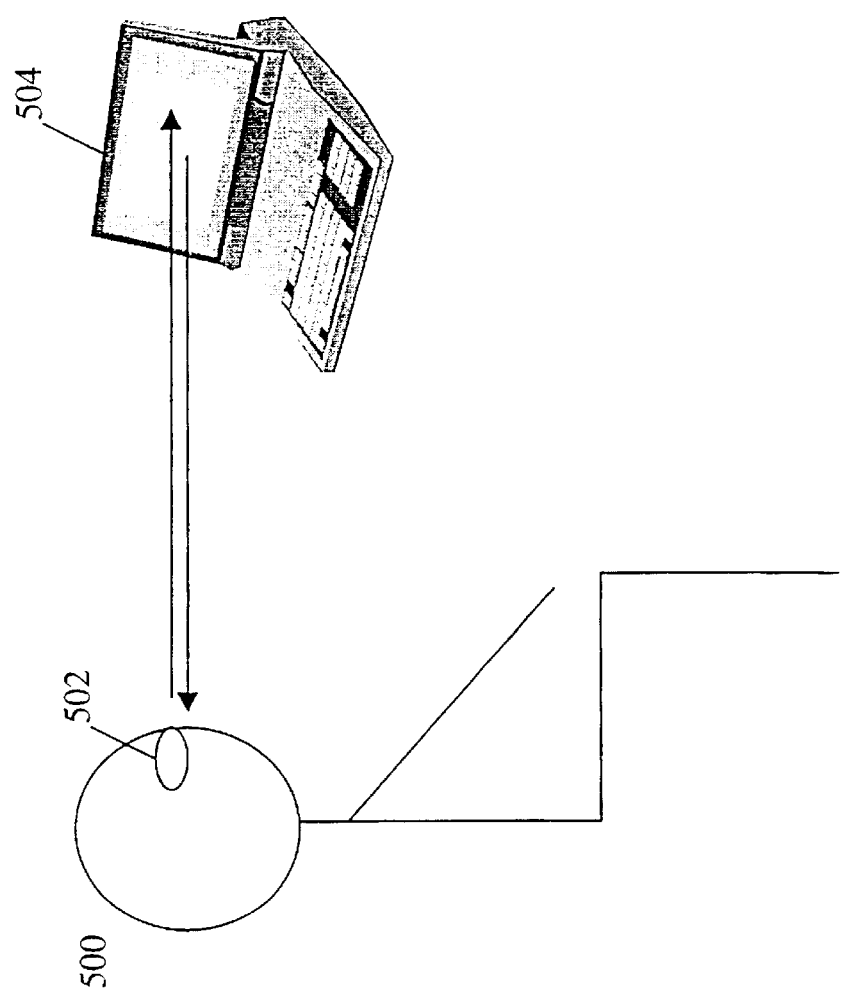
FIG. 5 depicts a typical use situation of the eye tracking device of the present invention.

FIG. 5 depicts an example of a typical use situation of the eye-gaze tracking and controlling device. In FIG. 5, a user or an observer 500 utilizes the eye-gaze tracking device integrated into a VRD device 504. A user's eye 502 is used to control VRD device 504.

After eye-gaze is mapped to VRD, VRD device 504 is in standby mode to utilize eye-gaze based controlling to the device used. Eye-gaze control can set a data stream delivering a high information content to the part of the display 504 that the eye 502 is gazing. Thus a control set or a control master is the eye-gaze itself functioning independently without any necessary need for additional control equipment. Also moreover, VRD display is divided into parts, which can provide more information or extra content when eye is gazed to the part of VRD display for a predetermined time period. Time period sets an idle for mapping the control according to part of VRD and prevents false gazes or quick gazes, which can be used to discern a scene of VRD.

Alternatively, a control set or a control master is eye-gaze combined to extra controlling equipment, such as a button, a mouse or a keyboard. After eye-gaze is mapped to VRD, VRD device 504 is in standby mode to utilize eye-gaze based controlling to the device used. Eye-gaze is in a part of VRD display, which user wants to have control, or in a part of VRD display, which is traditionally used to control the device, user confirms to utilize eye-gaze control by implementing an action using extra controlling equipment. Action can be a press of button or a keystroke indicating a mark to device to perform control, which happens in response to the user gazing at a button on the display. An exemplary angle accuracy is ten minutes of arc.

This paper presents the implementation and embodiments of the invention with the help of examples. It is obvious to a person skilled in the art, that the invention is not restricted to details of the embodiments presented above, and that the invention can be implemented in another embodiment without deviating from the characteristics of the invention. Thus, the presented embodiments should be considered illustrative, but not restricting. Hence, the possibilities of implementing and using the invention are only restricted by the enclosed patent claims. Consequently, the various options of implementing the invention as determined by the claims, including the equivalent implementations, also belong to the scope of the present invention.

For example, the mirror and the reflector have been described as having transparencies in order to integrate the device. However, it is possible to design and arrange the device in such a way, that the light from sources and the picture from the display panel will not meet concretely and will not disturb one another considerably.

For another example, after eye-gaze has been mapped on a display, the function has been for displaying a mark or setting a control. However, various applications can be implemented after mapping eye-gaze. A control can be set to another device, whose part VRD is, e.g., controlling a mechanical or electronic device utilizing embodiments of invention which is a part of the entire device.

What is claimed is:

1. A method of tracking eye-gaze, the method comprising
   emitting light having a certain wavelength;
   transferring the light to the retina of an eye;
   the certain wavelength of the light being such as to make the fovea of the eye clear, prominent, and resolvable;
   detecting light that is reflected from said eye to form detection information including the clear, prominent, and resolvable fovea;
   mapping the detection information to a predetermined surface, said predetermined surface being located at a distance from said eye, the location of the clear, prominent, and resolvable fovea on said predetermined surface forming an eye-gaze point.

2. The method of claim 1, wherein the light has a wavelength in the range of 395 nm to 500 nm.

3. The method of claim 1, wherein the light has a wavelength in the range of 395 nm to 430 nm.

4. The method of claim 1, wherein the light has a wavelength of 405 nm.

5. The method of claim 1, wherein the step of transferring the light comprises transferring the light within optics.

6. The method of claim 1, wherein the method comprises narrow band beam splitting at least one of the emitted and reflected light.

7. The method of claim 1, wherein the method comprises rotating the polarization 90 degrees of at least one of the emitted and reflected light.

8. The method of claim 1, wherein said detecting step comprises converting said light reflected from said eye retina to electronic information on a detector.

9. The method of claim 1, wherein said mapping comprises
   calculating a blood vessels pattern from said detection information;
   comparing said blood vessels pattern to a predetermined pattern;
   setting the location of the clear, prominent, and resolvable fovea on said predetermined surface based on said comparing step.

10. The method of claim 1, further comprising a step of displaying a mark on said predetermined surface at the eye-gaze point.

11. The method of claim 1, further comprising a step of performing a control function relating to the particular point of eye-gaze on the predetermined surface.

12. An eye-gaze tracking device, comprising:
   a light source for emitting light having a certain wavelength;
   means for transferring the light to the retina of an eye, the certain wavelength of the light being such as to make the fovea of the eye clear, prominent, and resolvable;
   a detector for detecting light that is reflected from said eye to form detection information including the clear, prominent, and resolvable fovea;
   a surface located at a distance from said eye; and
   means for mapping the detection information to the surface for locating the clear, prominent, and resolvable fovea on said surface for forming an eye-gaze point by the location of the clear prominent, and resolvable fovea.

13. The device of claim 12, wherein said surface includes a display.

14. The device of claim 12, further comprising a virtual reality display comprising a LCD panel.

15. The device of claim 12, further comprising imaging optics placed between said eye and said surface.

16. The device of claim 12, further comprising a control unit for transferring the detection information from said detector and for converting the detection information to said surface.

17. The device of claim 12, further comprising a narrow band reflector, a beam splitter and a narrow band mirror for reflecting and filtering the light at a narrow band in the range of said certain wavelength.

18. The device of claim 12, wherein said detector is a CCD (Charge Coupled Device) detector.

19. The device of claim 12, wherein said certain wavelength is within the range of 395 nm to 500 nm.

20. The device of claim 12, wherein said certain wavelength is within the range of 395 nm to 430 nm.

21. The device of claim 12, wherein said certain wavelength is 405 nm.

22. A mobile phone having an eye-gaze tracking device, comprising:
   a light source for emitting light falling within a certain wavelength range;
   means for transferring the light to the retina of an eye, the certain wavelength of the light being such as to make the fovea of the eye clear, prominent, and resolvable;
   a detector for detecting light that is reflected from said eye to form detection information including the clear, prominent, and resolvable fovea;
   a display located at a distance from said eye; and
   means for mapping the detection information to the display for locating the clear, prominent, and resolvable fovea on said display for forming an eye-gaze point by the location of the clear, prominent, and resolvable fovea.

23. The mobile phone having an eye-gaze device of claim 22, wherein the certain wavelength range is a narrowband blue wavelength range.

* * * * *